United States Patent
Hirsh et al.

(10) Patent No.: US 7,387,792 B2
(45) Date of Patent: *Jun. 17, 2008

(54) PHARMACEUTICAL COMPOSITION FOR COMPRESSED ANNULAR TABLET WITH MOLDED TRITURATE TABLET FOR BOTH INTRAORAL AND ORAL ADMINISTRATION

(75) Inventors: Jane C. Hirsh, Wellesley, MA (US); Kamal K. Midha, Hamilton (BM); Mark Hirsh, Wellesley, MA (US); Whe-Yong Lo, Canton, MA (US)

(73) Assignee: Collegium Pharmaceutical, Inc., Cumberland, RI (US)

( * ) Notice: Subject to any disclaimer, the term of this patent is extended or adjusted under 35 U.S.C. 154(b) by 119 days.

This patent is subject to a terminal disclaimer.

(21) Appl. No.: 11/041,474

(22) Filed: Jan. 24, 2005

(65) Prior Publication Data
US 2005/0123609 A1 Jun. 9, 2005

Related U.S. Application Data

(63) Continuation of application No. 10/015,930, filed on Nov. 30, 2001, now Pat. No. 6,863,901.

(51) Int. Cl.
A61K 9/20 (2006.01)
A61K 9/22 (2006.01)
A61K 9/24 (2006.01)
A61K 9/46 (2006.01)

(52) U.S. Cl. ............... 424/472; 424/464; 424/466; 424/468; 424/471; 424/473

(58) Field of Classification Search .............. None
See application file for complete search history.

(56) References Cited

U.S. PATENT DOCUMENTS

| | | |
|---|---|---|
| 2,297,599 A | 9/1942 | Wilen |
| 3,873,727 A | 3/1975 | Fusari et al. |
| 3,898,323 A | 8/1975 | Fennell et al. |
| 4,004,036 A | 1/1977 | Schmitt |
| 4,139,589 A | 2/1979 | Beringer et al. |
| 4,229,447 A | 10/1980 | Porter |
| 4,322,433 A | 3/1982 | Leslie et al. |
| 4,571,395 A | 2/1986 | Peck |
| 4,619,934 A | 10/1986 | Sunshine |
| 4,661,492 A | 4/1987 | Lewis et al. |
| 4,783,465 A | 11/1988 | Sunshine |
| 4,814,181 A | 3/1989 | Jordan et al. |
| 5,053,032 A | 10/1991 | Barclay et al. |
| 5,064,656 A | 11/1991 | Gergely et al. |
| 5,082,667 A | 1/1992 | Van Scoik |
| 5,156,850 A * | 10/1992 | Wong et al. ............ 424/473 |
| 5,248,310 A | 9/1993 | Barclay et al. |
| 5,294,433 A | 3/1994 | Singer et al. |
| 5,314,697 A | 5/1994 | Kwan |
| 5,362,496 A | 11/1994 | Baker et al. |
| 5,368,588 A | 11/1994 | Bettinger et al. |
| 5,369,588 A | 11/1994 | Hayami et al. |
| 5,385,941 A | 1/1995 | Fawzi |
| 5,407,339 A | 4/1995 | Fehlhafer |
| 5,407,686 A | 4/1995 | Patel et al. |
| 5,451,409 A | 9/1995 | Rencher et al. |
| 5,512,293 A | 4/1996 | Landrau et al. |
| 5,512,299 A | 4/1996 | Place et al. |
| 5,558,879 A | 9/1996 | Chen et al. |
| 5,573,776 A | 11/1996 | Harrison et al. |
| 5,595,997 A | 1/1997 | Aberg |
| 5,609,884 A | 3/1997 | Desai |
| 5,648,358 A | 7/1997 | Mitra |
| 5,656,284 A | 8/1997 | Balkin |
| 5,702,723 A | 12/1997 | Griffin |
| 5,739,136 A | 4/1998 | Ellinwood, Jr. et al. |
| 5,756,125 A | 5/1998 | Desai |
| 5,776,493 A | 7/1998 | Barclay et al. |
| 5,807,579 A | 9/1998 | Vilkov |
| 5,827,180 A | 10/1998 | Goodman |
| 5,827,852 A | 10/1998 | Russell |
| 5,900,421 A | 5/1999 | Handley |

(Continued)

FOREIGN PATENT DOCUMENTS

EP 0 584 594 3/1994

(Continued)

OTHER PUBLICATIONS

Hackhs, "Chemical Dictionary", 2nd Edition, pp. 185-186, Jun. 30, 1938.

(Continued)

Primary Examiner—S. Tran
(74) Attorney, Agent, or Firm—Pabst Patent Group LLP (57) ABSTRACT

New pharmaceutical compositions in unit dosage form are disclosed for both intraoral and oral administration to a patient, said unit dosage form configured to be placed intraorally of said patient, which comprises:
(a) as a first portion, at least one discrete molded triturate tablet comprising a therapeutically effective amount of at least one pharmaceutically active ingredient capable of intraoral administration; and
(b) as a second portion located around the said first portion, a therapeutically effective amount of at least one pharmaceutically active ingredient capable of oral administration and which is releasable and orally ingestible by the patient after the molded triturate tablet has disintegrated or has dissolved intraorally.

21 Claims, 1 Drawing Sheet

U.S. PATENT DOCUMENTS

| | | | |
|---|---|---|---|
| 6,004,582 A | 12/1999 | Faour et al. | |
| 6,039,974 A | 3/2000 | Maclaren | |
| 6,051,585 A | 4/2000 | Weinstein | |
| 6,054,463 A | 4/2000 | Handley | |
| 6,086,914 A | 7/2000 | Weinstein | |
| 6,110,500 A * | 8/2000 | Kim | 424/475 |
| 6,114,346 A | 9/2000 | Harris | |
| 6,124,320 A | 9/2000 | Woosley | |
| 6,130,233 A | 10/2000 | Woosley | |
| 6,166,037 A | 12/2000 | Budhu | |
| 6,183,778 B1 | 2/2001 | Conte et al. | |
| 6,294,199 B1 * | 9/2001 | Conley et al. | 424/468 |
| 6,372,254 B1 * | 4/2002 | Ting et al. | 424/473 |
| 6,372,255 B1 | 4/2002 | Saslawski et al. | |
| 6,379,651 B1 | 4/2002 | Athanikar | |
| 6,572,891 B1 * | 6/2003 | Ugarkovic | 424/489 |
| 6,602,518 B2 * | 8/2003 | Seielstad et al. | 424/439 |
| 6,863,901 B2 * | 3/2005 | Hirsh et al. | 424/472 |
| 2001/0002999 A1 * | 6/2001 | Neuser et al. | 424/464 |
| 2003/0143257 A1 * | 7/2003 | Fleshner-Barak et al. | 424/426 |

FOREIGN PATENT DOCUMENTS

| | | |
|---|---|---|
| EP | 1 044 680 | 10/2000 |
| EP | 1 112 737 | 7/2001 |
| FR | 2 772 615 | 6/1999 |
| GB | 800 973 | 9/1958 |
| WO | WO 99/15173 | 4/1999 |
| WO | WO 00/35296 | 6/2000 |
| WO | WO 01/37814 | 5/2001 |
| WO | WO 01/45688 | 6/2001 |
| WO | WO 98/46235 | 6/2001 |

OTHER PUBLICATIONS

Remington's Pharmaceutical Sciences, Eighteenth Edition, p. 844 (1990).

Onur Feyyaz, et al., "Simultaneous determination of pseudoephedrine sulfate dexbrompheniramine maleate and loratadine in pharmaceutical preparations using derivative spectrophotometry and ratio spectra derivative spectrophotometry", *Talanta*, 51(2):269-279 (2000).

* cited by examiner

COMPRESSED ANNULAR TABLET WITH MOLDED TRITURATE TABLET (CAT/T)

1 INTRAORAL PORTION
    MOLDED TRITURATE TABLET (T)

2 ORAL PORTION
    COMPRESSED ANNULAR TABLET (CAT)

PHARMACEUTICAL COMPOSITION FOR COMPRESSED ANNULAR TABLET WITH MOLDED TRITURATE TABLET FOR BOTH INTRAORAL AND ORAL ADMINISTRATION

CROSS-REFERENCE TO RELATED APPLICATIONS

This is a continuation of U.S. Ser. No. 10/015,930 filed Nov. 30, 2001 entitled "Pharmaceutical Composition for Compressed Annular Tablet with Molded Triturate Tablet for Both Intraoral and Oral Administration", by Jane C. Hirsh, Kamal K. Midha, Mark Hirsh, and Whe-Yong Lo.

FIELD OF THE INVENTION

This invention relates to a pharmaceutical composition that provides both for sublingual, buccal or vestibular mucosa or gingival application, hereafter referred to as intraoral administration and for chewed or sucked or swallowed hereafter referred to as oral administration. The pharmaceutical composition consists of two combined tablet portions, (1) a triturate tablet molded within the annulae of a second portion, and (2) a compressed tablet with a central cavity, hereafter referred to as a compressed annular tablet—CAT. The complete dosage form, hereafter referred to as compressed annular tablet with triturate tablet or CAT/T, comprises the triturate tablet molded into the compressed annular tablet through a manufacturing process. More particularly this invention relates to a triturate tablet composition containing at least one pharmaceutically active ingredient capable of intraoral administration and a compressed annular tablet with at least one pharmaceutically active ingredient capable of oral administration once the intraorally administered active ingredient has been substantially released. The invention further relates to a method of administering a pharmaceutical composition for both intraoral and oral administration to a patient. Furthermore, this invention combines two distinctly different pharmaceutical manufacturing processes to form one solid dosage unit: (1) employing dry powders or dried granulation to form a compressed annular tablet manufactured on a rotary tablet press, and (2) employing semi wet powders to form a molded triturate tablet manufactured on a tablet triturate machine.

BACKGROUND OF THE INVENTION

Intraoral administration of medicaments has been carried out according to the prior art. See U.S. Pat. No. 4,229,447 to PORTER. This patent discloses the intraoral administration of benzodiazepines including diazepam, lorazepam, oxazapam, temazapam, and chlordiazepoxide. According to Porter it is known in the art to administer benzodiazapines either orally or parenterally (i.e. by injection), especially intramuscularly or subcutaneously. Administering benzodiazepines by injection enables rapid attainment of effective plasma concentrations, that is more rapid than the plasma concentrations obtained following oral administration. One advantage of the intraoral administration as opposed to parenteral administration is that there is no injection site where pain and inflammation may develop. Another such advantage is that intraoral administration does not require sterilization of the preparations and the hypodermic syringes. Furthermore, in many situations self-administration of a medicament by parenteral means is not possible for a patient.

In U.S. Patent 5,739,136 to Ellinwood Jr. et al the medicament selected for intraoral administration is one that if given by oral administration is metabolized to an unwanted or aversive metabolite that is increasingly formed during gastrointestinal tract absorption and subsequent portal vein transport into the liver. Examples of such medicaments include not only the benzodiazepines especially a trifluorobenzodiazepine such as quazepam, but also other medicaments where it is advantageous to avoid first-pass metabolism such as the antianxiety/anticonvulsant/antihypnotic agents propoxyphene, nefazodone, trazodone, clomipramine, bupropion and combinations thereof. Unlike Porter, Ellinwood Jr. et al is not only concerned with rapidly attaining effective plasma concentrations of the intraorally administered medicament, but is especially concerned that the medicament include a drug where first pass-metabolism is to be avoided. The intraoral administration of the antianxiety/anticonvulsant/antihypnotic agents decreases the metabolism to the undesired metabolites.

In U.S. Pat. No. 6,183,778 to Jagotec AG, et al. the patent describes a multiple layer tablet capable of liberating one or more drugs at different release rates. This multi-layer dosage form is intended solely for oral administration and therefore must undergo first pass metabolism. Although it contains multiple releasing layers there is no dosage mechanism to provide the advantages presented by intraoral administration.

Remingtons, The Science and Practice of Pharmacy, 20th Ed., contains a complete history of dosage forms, including compressed tablets and triturate tablets; therefore, in the present invention no novelty is claimed in the broad practice of producing compressed tablets from dry powder or granulation or triturate tablets molded from a semi-wet powder. The uniqueness of the composition of this invention resides in its ability to provide in one dosage form the best features of both the compressed tablet and the triturate tablet.

The unique features of compressed tablets are well known in the art and is the dosage form most commonly employed as the method of choice for oral administration through which the tablets are digested and the drug absorbed into systemic circulation. Compressed tablets are not fragile and can withstand substantial handling without chipping or cracking. The compressed tablets can be formulated to provide disintegration and or dissolution of the active(s) at a specified time range after ingestion. They can be chewed but when used in this manner the tablets may lose some of their versatility. Compressed tablets can also be coated with a mixture containing a drug which will dissolve before the bulk of the tablet and may be absorbed intraorally. Compressed tablets may be layered, with one or more layers formulated to give early and rapid dissolution of drug in those layers as well as sustained dissolution of drugs in those layers. Compressed tablets may contain beads that are made of drugs in sustained-release or delayed-release forms in the tablet matrix.

Normally compressed tablets are uniformly solid but in this invention by employing tooling with a core rod, a ring shaped or annular tablet is produced, commonly referred to as a compressed annular tablet (CAT). Compressed tablets generally are intended to remain intact and not disintegrate until they reach the stomach or intestine. Compressed tablets are generally formulated with appropriate diluents or binders and/or polymers or waxes to obtain a desired appropriate hardness and are formulated as immediate, sustained or delayed released tablets.

Molded tablet triturates are, on the other hand, less versatile than compressed tablets. Tablet triturates usually are made from moist material comprising mainly one or more water soluble sugars. After the moist mass is incorporated in the mold to form a tablet triturate, the wet tablet triturates are ejected and dried. The resulting tablet triturates are generally more porous than the compressed tablets. Their main advantage is being rapidly disintegradable and soluble or dispersible in salivary fluid. They therefore lend themselves to intraoral administration and the avoidance of first pass metabolism. Triturate tablets have been more characterized by the disadvantages of friability or softness and thus require careful handling to prevent chipping and breaking particularly on their edges. In the present invention this disadvantage is overcome by molding and hence protecting the triturate tablet within center cavity of the compressed annular tablet, thereby eliminating the friability of the triturate while retaining the advantage of a rapidly soluble triturate tablet.

Nowhere in the literature is there a preparation of a triturate tablet which is molded within a compressed annular tablet.

Nowhere in the prior art references is there a disclosure of a pharmaceutical composition of a compressed annular tablet with a molded tablet triturate that effectively administers a therapeutically effective amount of pharmaceutically active ingredients by both intraoral means to obtain a rapid onset of desired therapeutic effect via plasma concentration and by oral means to obtain a more sustaining as well as complementary therapeutic effect.

OBJECTS OF THE INVENTION

It is an object of the invention to provide a pharmaceutical composition containing at least one pharmaceutically active ingredient capable of intraoral administration and at least one pharmaceutically active ingredient capable of oral administration and which is releasable and orally ingested by the patient after the pharmaceutically active ingredient capable of intraoral administration has disintegrated or has dissolved intraorally. It is a further object of the invention to provide a process for the preparation of a pharmaceutical composition containing at least one pharmaceutically active ingredient capable of intraoral administration and at least one pharmaceutically active ingredient capable of oral administration and which is orally ingested by the patient after the pharmaceutically active ingredient capable of intraoral administration has disintegrated or has dissolved intraorally.

It is a further object of the invention to provide a method of treatment employing a new pharmaceutical composition and dosage form which combines two portions, (1), a triturate tablet molded within the annular of the second portion (2), a compressed annular tablet (CAT). The complete dosage form, hereafter referred to as CAT/T comprises the triturate tablet molded into the compressed annular tablet through a unique manufacturing process.

It is a further object of this invention to provide a method of treatment with this new dosage form which has pharmaceutical compositions for both intraoral and oral administration that is easily administrable to a patient so as to maximize therapeutic effectiveness and minimize side effects.

SUMMARY OF THE INVENTION

We have found that the object of this invention can be achieved by a new pharmaceutical dosage form that combines both a triturate tablet, and a compressed annular tablet. The active ingredient for intraoral administration is contained in the first releasable portion, the triturate tablet which has been molded into the cavity of the second portion, a compressed annular tablet, which is designed to act as the mold to form the triturate tablet and also contains the active ingredients for oral administration. According to one feature the present invention is directed to a method of treating a patient by intraorally administering to the patient a therapeutically effective amount of a pharmaceutically active ingredient capable of intraoral administration. The second portion contains a therapeutically effective amount of a pharmaceutically active ingredient capable of oral administration which is orally ingested by the patient after the molded triturate tablet containing active ingredient capable of intraoral administration has disintegrated or has substantially dissolved intraorally. According to a preferred feature of the present invention, the pharmaceutical in unit dosage form is in the form, CAT/T, containing two portions; a compressed annular tablet, CAT, and molded triturate tablet, T, which is molded within the CAT.

The dosage unit for both intraoral and oral administration is configured to be placed intraorally and comprises:

(a) as a first releasable portion, one discrete triturate tablet (T) unit comprising a therapeutically effective amount of one or more pharmaceutically active ingredients capable of intraoral administration; and (b) as a second portion located around the first portion consisting of a compressed annular tablet (CAT) containing a therapeutically effective amount of at least one pharmaceutically active ingredient capable of oral administration and which is orally ingested by the patient after the molded triturate tablet has disintegrated or substantially dissolved intraorally.

The pharmaceutical dosage form of this invention may be administered preferably once or more times per day as well as administered in the morning (AM) or evening (PM). The dosage form contains, for intraoral dosing 1 mcg to 50 mg, preferably 5 mcg to 40 mg and more preferably 10 mcg to 30 mg pharmaceutically active ingredient capable of intraoral administration, and for oral dosing 5 mcg to 2 Gm, preferably 5 mg to 1000 mg and more preferably 10 mg to 500 mg of the pharmaceutically active ingredient capable of oral administration.

The present compositions are best suited where disease symptoms are such that both rapid relief of some of these symptoms are required as well as a continuation in controlling similar or other symptoms. Thus the molded triturate tablet unit containing pharmaceutical active ingredient(s) capable of intraoral administration provides rapid release for absorption of medicament for rapid relief of symptoms while the compressed annular tablet containing pharmaceutical active ingredient(s) capable of oral administration and releasing the medicament in an immediate or a sustained or delayed released manner to provide a continuation in control in similar or other symptoms. Thus the molded triturate tablet preferably contains a medicament suitable for intraoral administration in a dosage up to 30 mg and the molecular weight of the pharmaceutically active compound generally but not always does not exceed 350 daltons.

Another advantage of intraoral administration versus oral administration is the avoidance of first pass metabolism. Generally a pharmaceutical active compound for intraoral administration would have a lower bioavailability if given by oral administration. One of the reasons for the lower bioavailability for these orally administered pharmaceutically active compounds is that they undergo presystemic metabolism/clearance (i.e. first pass metabolism). These active ingredients are metabolized during their first passage through the gut wall and liver and thereby a significant fraction of the dose administered does not enter the bloodstream, and does not reach the receptors to exert activity. At times avoidance of presystemic metabolism results in avoiding the metabolism of the active drug into unwanted or aversive metabolites. At other times it allows lower doses of the active drug to provide desired activity as compared to oral dosing. Additionally, the presence or absence of food within the stomach and/or of the first portion of the small intestine may present erratic and/or unpredictable absorption of certain drugs. Thus the administration of medicament intraorally can avoid the food effect upon absorption.

The pharmaceutically active ingredients capable of intraoral administration and the pharmaceutically active ingredients capable of oral administration may include analgesics, antihistamines, antidiarrheal, anxiolytic, hypnotics, stimulants, cardiovascular drugs, pulmonary drugs, antihypertensives, antiemetics, anti-inflammatory drugs, renal drugs, steroids, drugs for neurological disorders, anticonvulsant drugs, drugs for treating endocrine disorders, drugs for sexual dysfunction, drugs for promoting immunology, drugs for treating osteoarthritis, drugs for treating glaucoma, drugs for treating allergic rhinitis, drugs for treating anemias and other hematological disorders, drugs for treating infectious diseases, drugs for the treatment and symptoms of cancer, drugs for insomnia, and antidiabetic drugs.

The pharmaceutically active ingredient capable of intraoral administration must be capable of being absorbed sublingually or buccally through mucous membranes of the oral cavity at its therapeutically effective level. Such an active ingredient may have a first pass metabolism that may be avoided by the intraoral administration and preferably has a rapid onset through the intraoral administration.

The pharmaceutically active ingredient capable of oral administration and orally administered may be the same as or may be different from the pharmaceutically active ingredient that is capable of intraoral administration and intraorally administered. The orally administered pharmaceutically active ingredient may be formulated as a chewable or swallowable form for immediate, sustained or delayed release of the pharmaceutical active compound. The sustained release action of the pharmaceutical active compound may range from 0.5 to 12 hours. A delayed release of the pharmaceutical active compound may also be effected from 0.5 to 12 hours after administration of the dosage unit.

The pharmaceutically active ingredient capable of oral administration and orally administered may be the same or may be a different pharmaceutically active ingredient from the intraorally administered pharmaceutically active ingredient of the molded triturate tablet. In the situation when the orally administered active pharmaceutical ingredient is different from the intraoral active pharmaceutical ingredient, it is intended to provide therapeutic benefit such as the relief of different symptoms of the same disease or to synergistically increase the total therapeutic effect of the individual pharmaceutically active ingredients. Depending upon the pharmaceutical active ingredient selected and the desired therapeutic effect to be achieved, this new dosage form can be formulated to be administered as needed at any time of the day or can be formulated for either morning (A.M.) or evening (P.M.) administration. For example, sedating and non-sedating antihistamines may be formulated into a dosage unit of this invention so that the sedating antihistamines, such as diphenhydramine or chlorpheniramine can be selected to be incorporated in the rapid release triturate portion and a non-sedating antihistamine such as loratadine may be selected for delayed release compressed annular tablet portion. Administration of such a dosage unit at or prior to bedtime provides rapid release of the sedating antihistamine in the triturate portion hence providing antihistaminic activity and additionally utilizing its sedating properties to aid in the onset of sleep. The non-sedating delayed release compressed tablet containing loratadine may be formulated to release loratadine 4 to 8 hours after ingestion of the dosage unit and thus be available upon waking for A.M. and day time therapeutic effect.

To summarize the features which can be unique for such a delivery system include:
1. Versatility which provides both rapid absorption through intraoral administration to avoid first pass metabolism as well as prolonged and(or) sustained absorption through the sustained or delayed release oral administration of the second portion.
2. Pharmacological complementarity.
3. Reduced dosage of the active ingredient by avoiding first pass metabolism.
4. Reduced side effects by avoiding the formation of undesired toxic metabolites.
5. P.M. or A.M. administration with clear advantages in terms of delivering medicament for specified time of the day for desired effect.
6. Improved compliance by administering two doses of one or more pharmaceutical active ingredient in one dosage form.

Examples of the pharmaceutically active ingredients capable of intraoral administration that are known in the art, based on their physicochemical, pharmacokinetic and pharmacodynamic properties are many. These active ingredients are not limited to those which include:

Buprenorphine, Butorphanol, Fenoprofen, Flurbiprofen, Diflunisal, Naproxen, Ibuprofen, Potassium Diclofenac, Fentanyl, Sodium Diclofenac, Parecoxib, Valdecoxib, Ketorolac, Tramadol, Bupropion, Aceclofenac, Acetaminophen, Acetanilide, Alphaprodine, Codeine, Dihydrocodeine, Dihydromorphine, Hydrocodone, Hydromorphone, Indoprofen, Ketoprofen, Ketorolac, Levorphanol, Loxoprofen, Meperidine, Methadone, Morphine, Naloxone, Pentazocine, Norlevorphanol, Oxycodone, Oxymorphone, Phenazocine, Propoxyphene, Tramadol, Zomepirac, Zolpidem, Zaleplon, Bupropion, Lorazepam, Buspirone, Ipsapirone, Gepirone, Triazolam, Nitrazepam, Estazolam, Diazepam, Oxazepam, Acetazolamide, Amiloride, Butazolamide, Clofenamide, Disulfamide, Ethacrynic Acid, Ethiazide, Ethoxzolamide, Etozolin, Fenquizone, Furosemide, Hydrochlorothiazide, Quinethazone, Torsemide, Triamterene, Cyproheptadine, Acravistine, Azatadine Maleate, Brompheniramine, Dextromethorphan, Carinoxamine Maleate, Chlorpheniramine, Descarboxyethyloratadine, Fexofenadine, Loratadine, Clemastine, Pseudoephedrine, Dexbrompheniramine, Diphenhydramine, Norastemizole, Doxylamine, Ketotifen, Promethazine, Tripelennamine, Plaunotol, Rosaprostol, Rotraxate, Spizofurone, Teprenone, Troxipide, Zolimidine, Temelastine, Naratriptan, Dizatriptan, Frovatriptan, Zolmitriptan, Sumatriptan, Almostriptan, Rizatriptan, Propanolol, Atenolol, Amitryptyline, Nortriptyline, Doxepin, Verapamil, Amlodipine, Ergotamine Tartrate, Caffeine, Dihydroergotamine, Bupropion, Methylphenidate, Captopril, Clonidine, Betaxolol, Bisoprolol, Nitroglycerin, Isorbide Mononitrate, Isosorbide Dinitrate, Bufuralol, Furosemide, Guanabenz, Guanfacine, Hydralazine, Labetalol, Metoprolol, Nadolol, Nifedipine, Oxprenolol, Pindolol, Sotalol, Timolol, Bunitrolol, Indecaimide, Nadoxolol, Penbutolol, Tocainide, Hydrochlorothiazide, Furosemide, Granisetron, Odansetron, Prochlorperazine, Metoclopramide, Clonazepam, Vigabatrin, Sildenafil, Alprostadil, Protriptyline, Trimiperamine, Imipramine, Desipramine, Azesetron, Batanopride, Zacopride, Bromopride, Acizapride.

To those skilled in the art, it is well known that physicochemical properties can be influenced by other inert agents which include penetration enhancers, pH modifiers and other taste masking agents to enhance intraoral administration).

Examples of the pharmaceutically active ingredients capable of oral administration not limited to but include: Bupropion, Rofecoxib, Fenoprofen, Flurbiprofen, Diflunisal, Naproxen, Ibuprofen, Indomethacin, Etodolac, Sulindac, Fentanyl, Sodium Diclofenac, Celecoxib, Parecoxib, Valdecoxib, Ketorolac, Tramadol, Aceclofenac, Acetanilide, Acetylsalcylsalicylic Acid, Alphaprodine, Aspirin, Bermoprofen, Naprosyn, Codeine, Dihydrocodeine, Dihydromorphine, Hydrocodone, Hydromorphone, Indoprofen, Ketoprofen, Ketorolac, Levorphanol, Loxoprofen, Mefenamic Acid, Meperidine, Methadone, Morphine, Nabumetone, Pentazocine, Norlevorphanol, Normethadone (N-desmethyl-methadone), Normorphine (N-desmethylmorphine), Oxycodone, Oxymorphone, Phenazocine, Propoxyphene, Salsalate, Suprofen, Tramadol, Zomepirac, Zolpidem, Zaleplon, Zopiclone, Hydroxyzine, Trazodone, Citalopram, Lorazepam, Buspirone, Ipsapirone, Gepirone, Triazolam, Nitrazepam, Estazolam, Diazepam, Oxazepam, Acetazolamide, Amanozine, Amiloride, Benzylhydrochlorothiazide, Bumetanide, Buthiazide, Chlorothiazide, Clofenamide, Clopamide, Clorexolone, Cyclothiazide, Disulfamide, Ethacrynic Acid, Ethiazide, Ethoxzolamide, Etozolin, Fenquizone, Furosemide, Hydracarbazine, Hydrochlorothiazide, Hydroflumethiazide, Indapamide, Mefruside, Methazolamide, Methyclothiazide, Metolazone, Pamabrom, Torsemide, Trimterene, Xipamide, Spironolactone, Cyproheptadine, Meclizine, Brompheniramine, Dextromethorphan, Citirizine, Chlorpheniramine, Descarboxyethylorati- dine, Fexofenadine, Loratadine, Pseudoephedrine, Dexbrompheniramine, Diphenhydramine, Norastemizole, Doxylamine, Ketotifen, Promethazine, Tripelennamine, Cimedtidine, Famotidine, Lansoprazole, Nizatidine, Omeprazole, Pantoprazole, Pirenzepine, Plaunotol, Ranitidine, Rebamipide, Rioprostil, Roxatidine Acetate, Telenzepine, Troxipide, Zolmidine, O-Desmethyl astemizole, Acrivastine, Temelastine, Naratriptan, Dizatriptan, Zolmitriptan, Sumatriptan, Almotriptan, Eletriptan, Rizatriptan, Propanolol, Atenolol, Amitryptyline, Nortriptyline, Doxepin, Verapamil, Amlodipine, Ergotamine tartrate, Caffeine, Dihydroergotamine, Amoxapine, Bupropion, Citalopram, Clomipramine, Desipramine, Doxepin, Fluoxetine, Fluvoxamine, Paroxetine, Trazodone, Vanlafaxine, d-amphetamine, Captopril, Enalapril, Lisinopril, Quinapril, Acebutolol, Benzapril, Nitroglycerin, Isorbide Mononitrate, Isosorbide Dinitrate, Bupranolol, Corvedilol, Condesortan, Diltiazem, Doxazosin, Felodipine, Fosinopril, Furosemide, Guanabenz, Guranfacine, Hydralazine, Indopamide, Irbesarton, Labetalol, Isradepine, Linopril, Losarton, Metolazone, Metoprolol, Mibefradil, Moexipril, Nadolol, Nicardipine, Nifedipine, Nisoldipine, Oxprenolol, Pindolol, Prazosin, Propranolol, Quinapril, Rampipril, Sotalol, Telmisartan, Temocapril, Terazosin, Trandolapril, Valsartan, Verapamil, Amiodarone, Aprindine, Bufetolol, Bunitrolol, Encainide, Flecainide, Indecamide, Mexiletine, Nadoxolol, Penbutolol, Practolol, Propafenone, Quinidine Sulphate, Tocainide, Bumetanide, Loperamide, Granistron, Dolasetron Mesylate, Ondansetron, Dexamethasone, Prochlorperazine, Metoclopramide, Gabapenten, Carbamazepine, Clonazepam, Lamotrigine, Phenyloin, Tigabine, Vigabatrin, Sildenafil, Papaverine, Azesetron, Cleopride, Batanopride, Itopride, Zacopride, Bromopride, Acizapride.

Pharmaceutically acceptable acid salts of the pharmaceutically active ingredient capable of intraoral administration or of the pharmaceutically active ingredient capable of oral administration and capable of forming pharmaceutically acceptable acid addition salts within the scope of this invention include the salts of any pharmaceutically acceptable inorganic acid or organic acid. Such inorganic acids may include: hydrochloric, hydrobromic, sulfuric, nitric or phosphoric acid. The organic acids may include acetic, propionic, glycolic, lactic, propyruvic, malonic, succinic, methanesulfonic, ethanesulfonic, benzenesulfonic, salicylic, malic, tartaric, maleic, fumaric, adipic, citric, ascorbic or cinnamic acid. The drugs with acidic functional groups may also include pharmaceutically acceptable salt-forming cations such as sodium, potassium or ammonium.

In the CAT/T for intraoral and oral administration the molded triturate tablet (T) contains a pharmaceutically active ingredient capable of intraoral administration and the CAT contains a pharmaceutically active ingredient capable of oral administration. The resulting pharmaceutical composition may be therapeutically effective over a duration of several hours up to 24 hours, especially where the pharmaceutically active ingredient capable of oral administration contained in the CAT is in sustained-release or delayed-release form.

Not only may the CAT contain an additional active ingredient capable of oral administration but furthermore the molded triturate tablet may also contain an additional pharmaceutically active ingredient capable of intraoral administration. In fact the CAT and the triturate tablet may both contain additional pharmaceutically active agents.

The triturate tablet for intraoral administration may include one or more pharmaceutically acceptable excipients such as but not limited to lactose, sucrose, dextrose, mannitol, starch, polyvinylpyrrolidone, microcrystalline, talc, sweeteners and flavoring agents. Other inert ingredients that may be included in the triturate tablet include solvents such as ethanol, polyethylene glycol, tetramethylene glycol, pentamethylene glycol, polyvinylpyrrolidones, mono-lower alkyl ethers of diethylene glycol and acetate esters of mono-lower alkyl ethers of diethylene glycol and purified water. The triturate blend may be prepared by mixing the pharmaceutical active ingredient(s) and the desired excipients in ethanol and/or water mixture to form a semi-moist powder mass.

The CAT may include, in addition to the pharmaceutically active ingredients capable of oral administration, pharmaceutically acceptable inert carriers such as, but not limited to, lactose, sucrose, dextrose, mannitol, microcrystalline cellulose, binding agents such as methyl cellulose, hydroxypropyl methylcellulose, polyvinylpyrrolidone, starch, acacia and other gums, glidants such as talc and colloidal silica, lubricant such as magnesium stearate and a flavoring agent. The CAT may contain one or more excipients such as methylcellulose, hydroxypropyl methylcellulose, ethyl cellulose, cellulose acetate phthalate, acacia, gums, wax, glycerol monostearate, acrylic acid polymers and copolymers, methacrylic acid, methyl acrylate, ethyl acrylate, methyl methacrylate, ethyl methacrylate for sustained release formulations and one or more ingredients such as methylcellulose, hydroxypropyl cellulose, hydroxyethyl cellulose, hydroxymethyl cellulose, hydroxypropyl methylcellulose, cellulose acetate succinate, ethylcellulose, cellulose acetate phthalate, cellulose acetate trimellitate, carboxymethyl cellulose sodium, acrylic acid polymers and copolymers, methacrylic acid, methyl acrylate, ethyl acrylate, methyl methacrylate, ethyl methacrylate, polyvinylpyrrolidone, vinyl acetate, vinyl acetate phthalate, azo compounds, pectin, amylose, shellac, zein, and guar gum for delayed release formulations.

In the manufacturing process, making the CAT is the essential first step in fabricating the complete dosage unit. The desired ingredients in the CAT are blended to form a dry blend and compressed into an annular tablet or the blend may first be granulated with a binder solution such as povidone in water, dried and milled to the desired particle size and then blended with a glidant and/or lubricant and then compressed into an annular tablet. The blend may contain sustained release excipients which may then be compressed into a sustained release CAT. The CAT may contain heads or pellets that are made with or are coated with sustained or delayed release material to sustain or delay the release of medicament in the beads. The CAT may be compressed using commercial high-speed rotary tablet machines equipped with punches having core rods. Typical tableting machines are Vector-Colton Model 216, Stokes/Pennwalt Model B3B, Kikusui Models Hercules and others. The CAT may be further coated with a sustained or delayed release material to delay the release of the contents of the compressed tablet. The CAT may also be applied with a film-coat for additional protection of the tablet. The finished dosage form may be manufactured by feeding the compressed annular tablet through a transfer chute which places the CAT onto the rotary driven molding plate of the tablet triturate machine and the CAT falls into the cavity of the plate. The CAT which is now inserted into the molding plate provides the annular mold for the triturate to be formed. A typical automated triturate machine such as the Vector Model 820 can be employed with modification to feed the CAT into the molding plate. In general, an automatic triturate machine includes a power feed station which supplies the triturate blend, a semi-wet powder, to the top surface of the molding plate. A tablet molding station provides for continuously spreading the semi-moist powder into the feed station housing the compressed annular tablet. The moist mass is pressed into the annuli of the CAT. An ejector station has lower punches which move the tablet molding plate so as to eject the CAT/T onto a conveyer where they are removed from the machine. The CAT/T should preferably be a flat faced tablet and suitable in size to be placed comfortably intraorally. The size of the CAT/T may vary depending on the drugs and doses to be administered. The outer diameter of the compressed annular tablet may range from 1/4" to 1" and more preferably 9/32" to 3/4" and more preferably 5/16" to 1/2". The diameter of the molded triturate tablet is dependent upon the diameter of the center cavity of the CAT and may range from a size of 7/16" or smaller more preferably 1/4" or smaller but minimally greater than 0.1". The thickness of the CAT/T will be approximately 1/10" or greater.

The dosage form is formulated so that the triturate disintegrates rapidly within 10 minutes and the patient is then instructed to chew or swallow the remainder of the dosage unit. The second portion of the composition, CAT which contains the pharmaceutically active ingredient capable of oral administration remains substantially intact and does not dissolve or disintegrate while the pharmaceutically active ingredient capable of intraoral administration is intraorally administered.

The invention further comprises a method of administering a pharmaceutical composition in unit dosage form for both intraoral and oral administration to a patient, which comprises:

(a) as a first releasing portion, a molded triturate tablet comprising a therapeutically effective amount of at least one pharmaceutically active ingredient capable of intraoral administration; and as a second portion located around the triturate tablet as a CAT, a therapeutically effective amount of at least one pharmaceutically active ingredient capable of oral administration and which is releasable and orally ingestible by the patient after the molded triturate tablet has disintegrated or has dissolved intraorally, comprising the steps of:

(i) placing the pharmaceutical dosage unit CAT/T intraorally;

(ii) retaining the pharmaceutical dosage CAT/T intraorally until the first portion, the molded triturate tablet containing the pharmaceutically active ingredient capable of intraoral administration has disintegrated or dissolved thereby substantially releasing the pharmaceutically active ingredient for intraoral absorption; and (iii) following step (ii) swallowing whole or chewing and swallowing the remaining dosage unit.

According to one feature of the invention the first portion of the compositions, the triturate tablet which contains the pharmaceutically active ingredient capable of intraoral administration disintegrates and/or dissolves rapidly, within 10 minutes, or shortly after the composition comes into contact with the patient's saliva. The second portion of the composition, CAT which contains the pharmaceutically active ingredient capable of oral administration remains substantially intact and does not dissolve or disintegrate while the pharmaceutically active ingredient capable of intraoral administration is intraorally administered.

Where it is desired to allow a rapid mucosal absorption of the pharmaceutically active ingredient capable of intraoral administration, the molded triturate tablet in the first portion containing the pharmaceutically active ingredient capable of intraoral administration will dissolve or disintegrate substantially immediately.

Once the triturate tablet in the first portion has dissolved or disintegrated, the second portion of the composition is either swallowed whole or chewed by the patient to release the pharmaceutically active ingredient capable of oral administration.

The present invention also relates to a process for the preparation of a pharmaceutical composition in unit dosage form as a CAT/T for both intraoral and oral administration to a patient, said pharmaceutical composition placed intraorally in said patient, which comprises:

(a) as a first release portion, at least one discrete molded triturate tablet comprising a therapeutically effective amount of at least one pharmaceutically active ingredient capable of intraoral administration; and (b) as a second portion located around the said first portion, a therapeutically effective amount of at least one pharmaceutically active ingredient capable of oral administration and which is releasable and orally ingestible by the patient after the triturate tablet has disintegrated or has dissolved intraorally. The preparation of the dosage unit comprises the steps of:

(i) preparing a triturate blend of pharmaceutically active ingredient and excipient blend which is moistened with ethanol or water or the mixture of;

(ii) preparing the second portion as a compressed annular tablet of at least one layer or a multi-layer CAT; and (iii) molding the first portion as a triturate tablet into the CAT.

The CAT unit may be coated prior to the molding of the triturate. The coating could be a film coat that is applied to the CAT. The film coat may comprise pharmaceutically acceptable coating polymers selected from the group consisting of cellulose, hydroxypropyl methylcellulose, methyl cellulose, polyvinylpyrrolidone, and polyethylene glycol, a pharmaceutically acceptable plasticizer, a pharmaceutically acceptable glidant and a pharmaceutically acceptable flavoring agent.

The molded triturate tablet comprises the pharmaceutically active compound for intraoral administration and is formulated with at least one pharmaceutically acceptable excipient for intraoral administration such as lactose, sugar, dextrose, mannitol, sorbitol, microcrystalline cellulose, starch, sodium starch glycolate, polyvinylpyrrolidone, polyethylene glycol, and magnesium stearate, talc, or a flavoring agents. Other inert ingredients that may be used in the inlaid triturate unit include solvents such as ethanol, polyethylene glycol, tetramethylene glycol, pentamethylene glycol, polyvinylpyrrolidones, mono-lower alkyl ethers of diethylene glycol and acetate esters of monolower alkyl ethers of diethylene glycol, or purified water.

Alternatively the molded triturate tablet comprising at least one pharmaceutically active ingredient capable of intraoral administration may contain at least one pharmaceutically acceptable effervescent agent such as an alkali carbonate or bicarbonate capable of rendering effervescence when contacted with water.

In any of the compositions disclosed herein above the molded triturate tablet may contain a pharmaceutically acceptable flavoring or taste masking agent. The CAT in one feature of the present invention is an immediate drug release tablet. Preferably the immediate release CAT comprises the pharmaceutically active ingredient capable of oral administration and is formulated with a conventional pharmaceutically acceptable excipient for oral administration such as lactose, sugar, mannitol, sorbitol, calcium sulfate, calcium phosphate dibasic, microcrystalline cellulose, methylcellulose, starch, sodium starch glycolate, polyvinylpyrrolidone, polyethylene glycol talc and magnesium stearate. The CAT may comprise one or more layers and where the CAT comprises multiple layers, one or more of the layers may contain the pharmaceutically active ingredient capable of oral administration in immediate release form.

In another feature of the present invention the CAT is a sustained drug release tablet which provides sustained release of the pharmaceutically active ingredient capable of oral administration. Preferably the sustained release effect lasts for 0.5 to 24 hours. The sustained drug release CAT comprises the pharmaceutically active ingredient capable of oral administration and is formulated with conventional pharmaceutically acceptable excipients for oral administration in sustained drug release form such as methylcellulose, hydroxypropyl methylcellulose, ethyl cellulose, cellulose acetate phthalate, acacia, gums, wax, glycerol monostearate, acrylic acid polymers and copolymers, methacrylic acid, methyl acrylate, ethyl acrylate, methyl methacrylate, ethyl methacrylate, and one or more conventional pharmaceutical excipients for oral administration such as lactose, calcium sulfate, calcium phosphate dibasic, sugar, microcrystalline cellulose, starch, sodium starch glycolate, polyvinylpyrrolidone, polyethylene glycol and magnesium stearate. In addition to formulating with the above sustained release excipients, the CAT may also be prepared with ion-exchange resins to form a sustained release complex. The CAT may comprise one or more layers. When the compressed tablet comprises multiple layers, one or more of the layers may contain the pharmaceutically active ingredient capable of oral administration in sustained release form.

In addition to pharmaceutical compositions where the CAT contains the pharmaceutically active ingredient capable of oral administration is in immediate release form or sustained release form, it is also within the scope of the invention that compositions of the CAT are coated with a delayed release coating, preferably delaying the release of medicament for 0.5 to 12 hours. The delayed release coating may be formulated with one or more pharmaceutically acceptable polymers selected from the group consisting of methylcellulose, hydroxypropyl cellulose, hydroxyethyl cellulose, hydroxymethyl cellulose, hydroxypropyl methylcellulose, cellulose acetate succinate, ethylcellulose, cellulose acetate phthalate, cellulose acetate trimellitate, carboxymethyl cellulose sodium, acrylic acid polymers and copolymers, methacrylic acid, methyl acrylate, ethyl acrylate, methyl methacrylate, ethyl methacrylate, polyvinylpyrrolidone, vinyl acetate, vinyl acetate phthalate, azo compounds, pectin, amylose, shellac, zein, and guar gum, in combination with a pharmaceutically acceptable plasticizer and a glidant. The pharmaceutical active ingredient may be formulated in beads or pellets and then enteric-coated with enteric coating polymers as described above. The enteric-coated beads or pellets may then be blended with other excipients and compressed into the CAT.

The CAT containing the pharmaceutically active ingredient capable of oral administration may be sucked, swallowed whole by the patient or may be in chewable form. The CAT may consist of multiple layers containing one or more pharmaceutically active ingredient capable of oral administration and may be in a chewable form. The CAT in chewable form or the CAT with multiple layers in chewable form comprises the pharmaceutically active ingredient capable of oral administration and a pharmaceutically acceptable excipient for chewable tablets selected from the group consisting of lactose, sorbitol, mannitol, sugar, starch, citric acid, tartaric acid, sweetening agent, magnesium stearate, and optionally with a flavoring agent.

The unique features of the delivery system of the invention includes pharmacological complementary, reduced side effects and versatility which provide immediate as well as sustained and prolonged therapeutic benefits along with improved patient compliance. For example, a patient with angina pectoris due to coronary artery disease may benefit from this dosage form, when the triturate provides immediate onset of activity from intraoral nitroglycerin for acute relief and prophylaxis in life threatening situations of an acute angina attack and sub sequentially the availability of oral delayed isorbide mononitrate sustained release for angina pectoris prevention. This provides the patient immediate relief from the acute angina attack and at the same time the benefit of continued prevention from angina pectoris up to approximately 12 hours.

BRIEF DESCRIPTION OF THE DRAWING

The sole FIGURE in this application is a perspective drawing cut in section and which shows the tablet.

Figure 1:
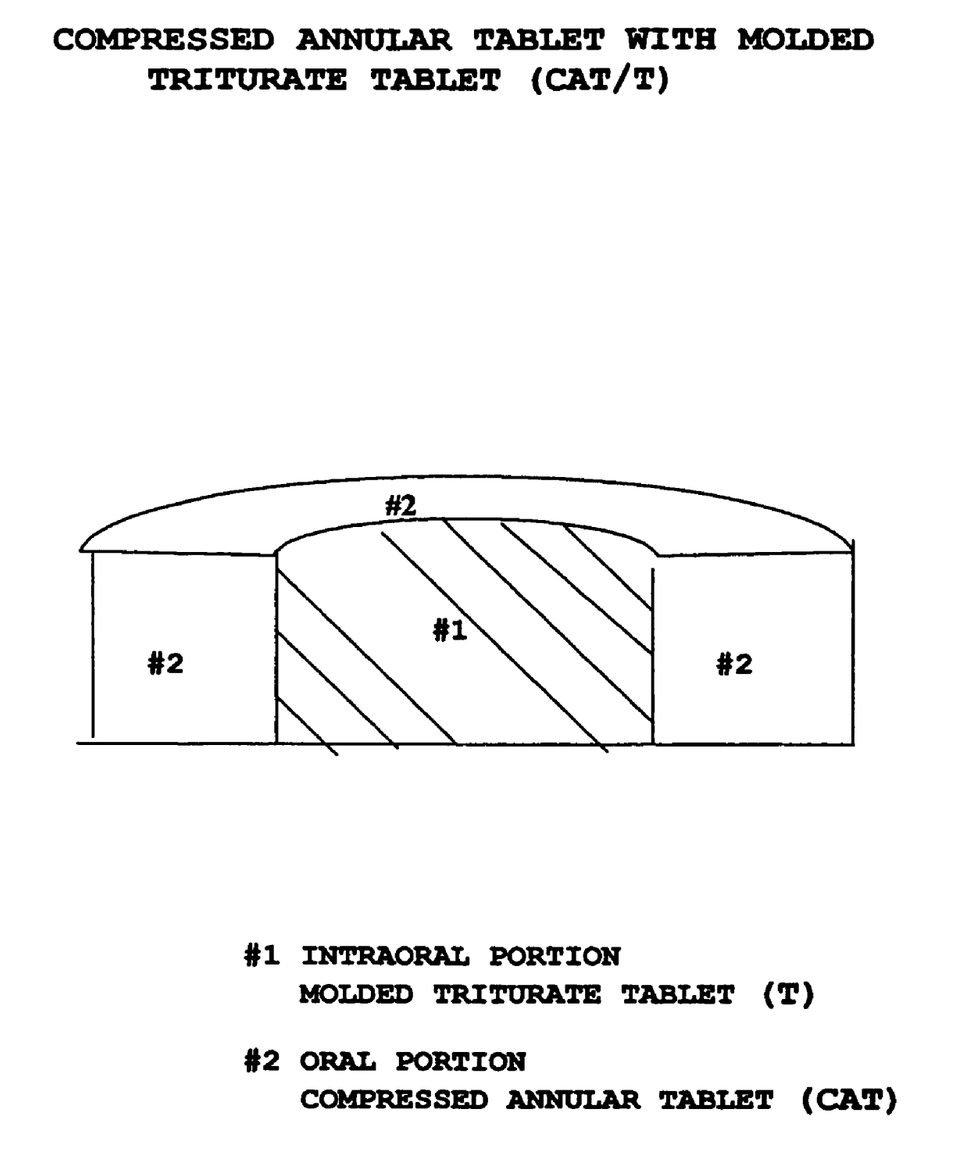

The drawing shows the compressed tablet with a central cavity and an inlaid triturate where the first portion—which is an inlaid triturate 1 suitable for intraoral administration. The second portion 2, suitable for oral administration, comprises a compressed tablet with a central cavity which surrounds the inlaid triturate.

An important feature of this dosage form is that the disintegration of the molded triturate tablet signals the patient to swallow the remaining portion, the CAT, or after a specified time the patient is instructed to swallow or chew the CAT and thus the CAT is administered just as any conventional oral medication once the molded triturate has disintegrated.

It is common to add a flavoring agent to a medicament that is intraorally administered. The molded triturate may contain such a flavoring agent dispersed throughout to make the intraoral administration more pleasant to the patient. Where there is such a flavoring agent in the molded triturate, there may the same or different flavor in CAT.

COMPRESSED ANNULAR TABLET WITH MOLDED TRITURATE TABLET, CAT/T.

EXAMPLES

Example 1

Anti-Migraine Agent—Zolmitriptan 1.25 to 2.5 mg Immediate Release and Zolmitriptan 1.25 to 2.5 mg in Delayed Release (A) Preparation of Zolmitriptan CAT:
  (a) Preparation of Zolmitriptan Beads:

| Ingredients | % Weight | Typical Example mg/unit |
|---|---|---|
| Zolmitriptan | 1-10 | 1.25 |
| Talc | 0.1-5 | 0.12 |
| Polyvinylpyrrolidone | 0.1-5 | 0.12 |
| Water/ethanol | (To be evaporated) | (To be evaporated) |
| Sugar spheres | 80-98 | 60 |
| Sub Total | | 61.49 |

Procedure (1) Prepare a dispersion containing Zolmitriptan and talc in polyvinylpyrrolidone solution prepared in water and/or ethanol or a mixture thereof.
(2) Apply or spray solution (1) onto the sugar spheres using a coating pan or a fluid bed coater until a desired amount of solution (1) is applied.
(3) The coated spheres may be further seal-coated with a solution containing polyvinylpyrrolidone prepared in water and/or ethanol or a mixture thereof.
  (b) Preparation of Enteric Coated Zolmitriptan Beads:

| Ingredients | % Weight | Typical Example mg/unit |
|---|---|---|
| Eudragit S100 | 2-15 | 6.0 |
| Triethyl citrate | 1-7 | 3.0 |
| Talc | 0.5-4 | 1.5 |
| Ammonium (As 1N (3.5%) ammonium hydroxide solution) | 0.05-0.3 | 0.105 (3.0 ml 1N Solution) |
| Water | (To be evaporated) | (To be evaporated) |
| Zolmitriptan beads (step (a)) | 70-95 | 61.49 |
| Sub Total | | 72.09 |

Procedure (1) Prepare the coating solution by mixing water, Eudragit S100, ammonium hydroxide solution, triethyl citrate and talc to form a uniform dispersion.
(2) Coat Zolmitriptan beads (from (a)) with Eudragit S coating solution using a coating pan or a fluid bed coater until a desired coat weight is achieved.
  (c) Seal Coat of the Enteric Coated Zolmitriptan Beads:

| Ingredients | % Weight | Typical Example mg/unit |
|---|---|---|
| Hydroxypropyl methylcellulose | 2-15 | 3.1 |
| Polyethylene glycol | 0.2-4 | 0.4 |
| Optional Flavoring agent | 0.2-5 | 0.5 |
| Optional coloring agent | 0.2-5 | 0.5 |
| Water or ethanol | (To be evaporated) | (To be evaporated) |
| Zolmitriptan Enteric Coated beads (step b) | 85-97 | 72.09 |
| Sub Total | | 76.59 |

Procedure (1) Prepare a coating solution of Hydroxypropyl methylcellulose and polyethylene glycol in water or ethanol or combination thereof.
(2) Coat Zolmitriptan Enteric Coated beads (step (b)) with the above coating solution in a coating pan or a fluid bed coater until a desired coating weight is obtained.
  (d) Preparation of Zolmitriptan CAT:

| Ingredients | % Weight | Typical Example mg/unit |
|---|---|---|
| Lactose monohydrate | 20-60 | 100 |
| Microcrystalline cellulose | 15-35 | 60 |
| Polyvinylpyrrolidone | 2-10 | 10 |
| Flavoring agent (s) | 0.5-5 | 5 |
| Magnesium Stearate | 0.2-2.0 | 1.0 |
| Zolmitriptan Enteric Coated beads (step c) | 20-50 | 76.59 |
| Sub Total | | 253.59 |

Procedure (1) Prepare a granulation blend of lactose, microcrystalline cellulose, polyvinylpyrrolidone and flavoring agent. Blend with Zolmitriptan Enteric Coated beads (step (c)) and final blend with magnesium stearate.
(2) Compress the granulation blend into a CAT using compression tooling and tabletting apparatuses.

(B) Preparation of Zolmitriptan Triturate Blend:

| Ingredients | % Weight | Typical Example mg/unit |
|---|---|---|
| Zolmitriptan | 1-5 | 1.25 |
| Lactose, fine powder | 50-90 | 55 |
| Sucrose, fine powder | 10-40 | 10 |
| Flavoring agent | 0.5-5 | 1 |
| Polyvinylpyrrolidone | 0.05-1 | 0.05 |
| Ethyl alcohol, 95% | (To be evaporated) | — |
| Water | (To be evaporated) | — |
| Sub Total | | 67.3 |

Procedure (1) Prepare the solvent mixture containing polyvinylpyrrolidone, ethyl alcohol and water.
(2) Blend Zolmitriptan, lactose, sucrose and the flavoring agent. Screen to break lumps.
(3) Add (1) to (2) while mixing until a moistened powder blend is achieved.

(C) Preparation of Molded Triturate into the CAT/T—The Finished Product (CAT/T)

| Ingredients | % Weight | Typical Example mg/tablet |
|---|---|---|
| Zolmitriptan CAT (A) | 70-90 | 253.59 |
| Zolmitriptan Triturate Blend (B) | 10-30 | 67.3 |
| Total (Finished product) | | 310.89 |

Procedure (1) Prepare the finished dosage form by triturating (B) into the center hole of the CAT (A) using an apparatus capable of molding triturate into the center cavity of the CAT.

(D) Description of the Finished Dosage Design (CAT/T)

The product contains 1.25 mg Zolmitriptan in the molded triturate tablet for intraoral release and 1.25 mg Zolmitriptan in the delayed release beads which are incorporated in the matrix of CAT unit. Enteric coated Zolmitriptan starts to release 2 to 4 hours after oral administration of the dosage form. The patient is instructed to take the dosage unit (CAT/T) intraorally where the molded triturate tablet disintegrates rapidly resulting in the release of the drug for rapid intraoral absorption. Once the disintegration of triturate tablet is complete the patient may swallow the remainder of the dosage unit, the CAT, which will then release release the second part of the medicine 2-4 hours after administration of the dosage unit. The dosage form provides initial rapid onset of Zolmitriptan from the triturate tablet portion of the dosage unit and also provides a second dose of Zolmitriptan 2 to 4 hours after the dosage administration for a total of about 4 to 5 hours treatment in migraine headaches.

Example 2

Antiemetic and Narcotic Formulation—Granisetron Hydrochloride 1.12 mg (Equivalent to 1 mg Base) for Intraoral Administration and Morphine Sulfate 30 to 120 mg in Sustained Release for Oral Administration (A) Preparation of Morphine Sulfate Sustained Release CAT:

| Ingredients | % Weight | Typical Example mg/unit |
|---|---|---|
| Morphine sulfate | 10-25 | 30 |
| Hydroxypropyl Methylcellulose | 45-65 | 130 |
| Lactose monohydrate | 20-40 | 70 |
| Polyvinylpyrrolidone | 3-10 | 10 |
| Silicone dioxide | 0.3-1.5 | 2 |
| Stearic acid | 0.3-1.5 | 2 |
| Sub Total | | 244 |

Procedure (1) Prepare a granulation blend containing Morphine sulfate, hyproxypropyl methylcellulose, lactose and polyvinylpyrrolidone. Add silicon dioxide and stearic acid to the granulation and blend for additional 5 to 10 minutes.
(2) Compress the above Morphine sulfate sustained release granulation into CAT unit using appropriate tooling and tabletting apparatuses.

(B) Preparation of Granisetron Triturate Blend

| Ingredients | % Weight | Typical Example mg/unit |
|---|---|---|
| Granisetron hydrochloride | 1-5 | 1.12 |
| Lactose, fine powder | 60-95 | 60 |
| Sucrose, fine powder | 5-20 | 5 |
| Flavoring agent | 0.5-5 | 1 |
| Polyvinylpyrrolidone | 0.05-1 | 0.06 |
| Ethyl alcohol, 95% | (To be evaporated) | — |
| Water | (To be evaporated) | — |
| Sub Total | | 67.18 |

Procedure (1) Prepare the solvent mixture containing polyvinylpyrrolidone in water or a mixture of water and ethanol.
(2) Blend Granisetron hydrochloride, lactose, sucrose and the flavoring agent. Screen to break lumps.
(3) Add (1) to (2) while mixing until a moistened powder blend is achieved.

(C) Preparation of Molded Triturate Tablet into the CAT—The Finished Product CAT/T

| Ingredients | % Weight | Typical Example mg/tablet |
|---|---|---|
| Morphine sulfate Sustained release CAT (A) | 70-90 | 244 |
| Granisetron Triturate Blend (B) | 10-30 | 67.18 |
| Total (Finished product) | | 311.18 |

Procedure

Prepare the finished dosage form by pressing the semi-moist triturate blend (B) into the center cavity of the CAT (A) using suitable equipment capable of molding triturate tablets into the center cavity of a CAT.

(D) Description of the Dosage Unit Design:

The product contains 1.12 mg Granisetron hydrochloride in the molded triturate tablet for intraoral release and 30 mg morphine sulfate in the matrix of CAT unit as a sustained release form which releases morphine for a period of 8 to 12 hours. The patient is instructed to take the dosage unit (CAT/T) intraorally where the molded triturate tablet disintegrates rapidly resulting in the release of Granisetron for rapid intraoral absorption. Once the disintegration of molded triturate tablet is complete the patient may swallow the remainder of the dosage unit, the CAT, which will then release morphine in a sustained release for 8 to 12 hours. Nausea and vomiting is a common adverse reaction associated with administration of morphine and other narcotic analgesics. The administration of an antiemetic agent such as Granisetron prior to the administration of a narcotic analgesic prevents the nausea and vomiting side effects.

Example 3

Sedating and Non-sedating Antihistamine—Chlorpheniramine Maleate 2 to 4 mg for Intraoral Administration and Loratadine 5 to 7 mg in Delayed Release Form for Oral Administration (A) Preparation of Loratadine CAT:

| Ingredients | % Weight | Typical Example mg/unit |
|---|---|---|
| Loratadine | 2-5 | 5 |
| Lactose monohydrate | 60-70 | 141.5 |
| Microcrystalline cellulose | 25 | 55 |
| Starch | 10 | 22 |
| Magnesium stearate | 0.5 | 1.5 |
| Sub Total | | 225 |

Procedure (1) Prepare a granulation containing Loratadine, lactose, Microcrystalline cellulose and starch.
(2) Blend with magnesium stearate for 5 minutes.
(3) Compress the above granulation into CAT unit using tooling and tabletting apparatuses.

(B) Preparation of Enteric Coated Loratadine CAT:

| Ingredients | % Weight | Typical Example mg/unit |
|---|---|---|
| Eudragit S100 | 4-12 | 18 |
| Triethyl citrate | 1-6 | 9 |
| Talc | 0.5-5 | 4.5 |
| Ammonium (As 1N (3.5%) ammonium hydroxide solution) | 0.05-0.5 | 0.315 (9 ml 1N solution) |
| Water | (To be evaporated) | (To be evaporated) |
| Loratadine CAT (step (A)) | 80-97 | 225 |
| Sub Total | | 256.8 |

Procedure (1) Prepare the coating solution by mixing water, Eudragit S100, ammonium hydroxide solution, triethyl citrate and talc to form a uniform dispersion.
(2) Coat Loratadine CAT unit (from (A)) with Eudragit S coating solution using a coating pan or a fluid bed coater until a desired coat weight is achieved.

(C) Seal Coat of the Enteric Coated Loratadine CAT Unit:

| Ingredients | % Weight | Typical Example mg/unit |
|---|---|---|
| Eudragit EPO | 2-15 | 14.0 |
| Citric acid | 1-6 | 8 |
| Water | (To be evaporated) | (To be evaporated) |
| Loratadine Enteric Coated CTCC (step (B)) | 90-98 | 256.8 |
| Sub Total | | 278.8 |

Procedure (1) Prepare a coating solution containing Eudragit E and citric acid in water.
(2) Coat Loratadine Enteric Coated CAT unit (step (B)) with the above coating solution in a coating pan or a fluid bed coater until a desired coating weight is obtained.

(D) Preparation of Chlorpheniramine Maleate Triturate Blend:

| Ingredients | % Weight | Typical Example mg/unit |
|---|---|---|
| Chlorpheniramine maleate | 1-5 | 4 |
| Lactose, fine powder | 50-90 | 45 |
| Sucrose, fine powder | 10-40 | 15 |
| Flavoring agent | 0.5-5 | 2 |
| Polyvinylpyrrolidone | 0.05-1 | 0.1 |
| Ethyl alcohol, 95% | (To be evaporated) | (To be evaporated) |
| Water | (To be evaporated) | (To be evaporated) |
| Sub Total | | 66.1 |

Procedure (1) Prepare the solvent mixture containing polyvinylpyrrolidone, ethyl alcohol and water.
(2) Blend Chlorpheniramine maleate, lactose, sucrose and flavoring agent. Screen to break lumps.
(3) Add (1) to (2) until a moistened powder blend is achieved.

(E) Preparation of Molded Triturate into the CAT—The Finished Product (CAT/T)

| Ingredients | % Weight | Typical Example mg/tablet |
|---|---|---|
| Loratadine enteric coated CAT (C) | 70-90 | 278.8 |
| Chlorpheniramine maleate Triturate Blend (D) | 10-30 | 66.1 |
| Total (Finished product) | | 344.9 |

Procedure

Prepare the finished dosage form by pressing the semi-moist triturate blend (D) into the center cavity of the CAT (C) using an apparatus capable of molding triturate tablets into the center of the CAT.

(F) Description of the Dosage Unit Design (CAT/T):

The product contains 4 mg of Chlorpheniramine maleate in the molded triturate tablet for intraoral release and 5 mg of Loratadine in the delayed release form as incorporated in the matrix of CAT. Enteric coated Loratadine starts to release 4 to 8 hours after administration of the dosage form.

The patient is instructed to take the dosage unit intraorally where the molded triturate tablet disintegrates rapidly resulting in the release of chlorpheniramine maleate for rapid intraoral absorption. Once the disintegration of the triturate tablet is complete the patient may swallow the remainder of the dosage unit, the CAT, which will then release the second part, loratadine, 4 to 8 hours after administration of the dosage unit. The patient is instructed to take the antihistamine dosage form in the evening prior to bedtime. As a result of the dosage design, the sedating antihistamine is released substantially immediately through intraoral administration for providing night time antihistamine activity and sedation and the non-sedating antihistamine will be released 4 to 8 hours later for day time antihistaminic activity.

Example 4

Anti-Angina Formulation—Nitroglycerin 0.3 to 0.6 mg for Intraoral Administration and Isosorbide Mononitrate 30 to 120 mg in Sustained Release for Oral Administration (A) Preparation of Isosorbide Mononitrate Sustained Release CAT:

| Ingredients | % Weight | Typical Example mg/unit |
|---|---|---|
| Isosorbide mononitrate | 10-25 | 30 |
| Hydroxypropyl Methylcellulose | 30-60 | 100 |
| Lactose monohydrate | 10-25 | 40 |
| Ethylcellulose | 10-25 | 40 |
| Polyvinylpyrrolidone | 5-15 | 18 |
| Silicone dioxide | 0.3-1.5 | 2 |
| Stearic acid | 0.3-1.5 | 2 |
| Magnesium stearate | 0.1-1.0 | 1 |
| Sub Total | | 233 |

Procedure (1) Blend Isosorbide Mononitrate, hyproxypropyl methylcellulose, ethylcellulose and lactose to form a uniform blend.
(2) Prepare polyvinylpyrrolidone in water or a mixture of water and ethanol solution.
(3) Granulate step (1) with solution from step (2). Dry the Granulation and screen or mill to desired particle size.
(4) Add silicon dioxide, stearic acid and magnesium stearate and blend for additional 5 to 10 minutes.

Compress Isosorbide sustained release CAT unit using tooling and tabletting apparatuses.

(B) Preparation of Delayed Release Isosorbide CAT

| Ingredients | % Weight | Typical Example Mg/tablet |
|---|---|---|
| Eudragit L 100-55 | 3-8 | 18 |
| Triethyl citrate | 0.3-2 | 1.8 |
| Talc | 0.5-3 | 4.5 |
| Polyethylene glycol 6000 | 0.2-2 | 1.47 |
| Sodium hydroxide | 0.05-0.2 | 0.29 |
| Water | (To be evaporated) | — |
| Isosorbide Mononitrate CAT (A) | 85-98 | 233 |
| Sub Total | | 259.06 |

Procedure (1) Prepare the coating solution by mixing water, Eudragit L 100-55, Sodium hydroxide, PEG 6000, triethyl citrate and talc to form a uniform dispersion.
(2) Coat Isosorbide Mononitrate CAT (from (A)) with Eudragit L coating solution using a coating pan or a fluid bed coater until a desired coat weight is achieved.

(C) Seal Coat of the Enteric Coated Isosorbide CAT:

| Ingredients | % Weight | Typical Example mg/unit |
|---|---|---|
| Eudragit EPO | 2-15 | 14.0 |
| Citric acid | 1-6 | 8.0 |
| Water | (To be evaporated) | (To be evaporated) |
| Isosorbide mononitrate Enteric Coated CAT (step (B)) | 90-98 | 259.06 |
| Sub Total | | 281.06 |

Procedure (1) Prepare a coating solution containing Eudragit E and citric acid in water.
(2) Coat Isosorbide Mononitrate Enteric Coated CAT unit (step (B)) with the above coating solution in a coating pan or a fluid bed coater until a desired coating weight is obtained.

(D) Preparation of Nitroglycerin Semi-moist Triturate Blend:

| Ingredients | % Weight | Typical Example mg/tablet |
|---|---|---|
| Nitroglycerin | 0.2-5 | 0.3 |
| Lactose, fine powder | 70-95 | 65 |
| Sucrose, fine powder | 2-20 | 5 |
| Flavoring agent | 0.5-5 | 2 |
| Polyvinylpyrrolidone | 0.05-1 | 0.1 |
| Ethyl alcohol, 95% | (To be evaporated) | — |
| Water | (To be evaporated) | — |
| Sub Total | | 72.4 |

Procedure (1) Prepare the solvent mixture containing polyvinylpyrrolidone, ethyl alcohol and water.
(2) Blend Nitroglycerin, lactose, sucrose and the flavoring agent. Screen to break lumps.
(3) Add (1) to (2) until a moistened powder blend is achieved.

(E) Preparation of Molded Triturate Tablet into the CAT— The Finished Product (CAT/T)

| Ingredients | % Weight | Typical Example mg/tablet |
|---|---|---|
| Isosorbide mononitrate Enteric Coated Sustained release CAT (B) | 70-90 | 281.06 |
| Nitroglycerin Triturate Blend (C) | 10-30 | 72.4 |
| Total (Finished product) | | 353.46 |

Procedure

Prepare the finished dosage form by pressing the semi-moist triturate blend (C) into the center cavity of the CAT(B) using an apparatus capable of molding triturate tablets into a CAT.

(F) Description of the Dosage Unit Design:

The product contains 0.3 mg nitroglycerin in the molded triturate tablet for intraoral release and 30 mg Isosorbide Mononitrate in the CAT as a sustained release form which releases Isosorbide for a duration of 8 to 12 hours. The Isosorbide sustained release CAT unit is further coated with delayed release formulation so that the sustained released Isosorbide CAT starts to release 1 to 2 hours after administration of the dosage form.

The patient is instructed to take the dosage unit intraorally where the molded triturate tablet disintegrates rapidly resulting in the rapid release of the drug for intraoral absorption. Once the disintegration of molded triturate tablet is complete the patient may swallow the remainder of the dosage unit, the CAT, which will then release Isosorbide Mononitrate 1 to 2 hours later for a sustained release duration of 8 to 12 hours. The initial immediate release of Nitroglycerin from the triturate provides a rapid onset to prevent acute angina attack due to coronary artery disease for a duration of about 30 minutes to 1 hour at which time the delayed and sustained release Isosorbide Mononitrate CAT starts to release and provides a duration of 8 to 12 hours therapeutic intervention for prophylactic effect for angina.

REFERENCES

1. U.S. Pat. No. 5,407,339, Triturate Tablet Machine. Fehlhafer, J. E. Apr. 18, 1995.
2. U.S. Pat. No. 3,873,727, Stabilization of molded sublingual nitroglycerin tablets. Fusari, S. A. Mar. 25, 1975.
3. U.S. Pat. No. 5,739,136, Intraoral dosing method of administering medicaments. Ellinwood Jr. Apr. 14, 1998.
4. U.S. Pat. No. 4,229,447, Intraoral methods of using benzodiazepines. W. R. Porter. Oct. 21, 1980.
5. U.S. Pat. No. 6,183,778, Pharmaceutical tablet capable of liberating one or more drugs at different release rates. Conte, et al. Feb. 6, 2001
6. U.S. Pat. No. 4,004,036, Effervescent molded triturate tablets. Schmitt. Jan. 18, 1977.
7. AHFS Drug Information 2000.
8. Mosby's GenRx, 11th Ed. (2001).
9. USP DI Vol. 1—Drug Info. For the Health Care Pro., 21st Ed. (2001).
10. USP DI Vol. II—Advice for the Patient, 21st Ed. (2001).
11. Ellenhorn's Medical Toxicology, 2nd Ed. (1994).
12. Griffith's 5 Minute Clinical Consult., 9th Ed (2001). 13. The Merck Manual, 17th Ed. (1999).
14. Current Diagnosis & Treatment in Cardiology, 1st Ed. (1995).
15. Current Critical Care Diagnosis & Treatment, 1st Ed. (1994).
16. Textbook of Organic Medicinal & Pharmaceutical Chemistry, 10th Ed. 1998
17. The Complete Drug Reference, Martindale, 32nd Ed. 1999. 18. The Merck Index, 12th Ed. 1996.
19. Pharmacotherapy A Pathosphysiologic Approach, 4th Ed. 1999.
20. Pharmacology, 2nd Ed. Lippincott's Illustrated Reviews. 1997.

What is claimed is:

1. A pharmaceutical composition which comprises:
  (a) an intraorally first releasing portion, in the form of a tablet comprising a therapeutically effective amount of at least one pharmaceutically active ingredient capable of intraoral administration having a molecular weight of less than 350 Daltons, in a dosage of no more than 50 mg, wherein the tablet comprises an excipient and disintegrates or dissolves within 10 minutes permitting rapid release and uptake of the pharmaceutically active ingredient within the oral region; and
  (b) a second releasing portion located around the first portion, comprising a therapeutically effective amount of at least one pharmaceutically active ingredient capable of oral administration and which is releasable and orally ingestible by the patient after the tablet of (a) has disintegrated or has dissolved intraorally wherein it is absorbed after swallowing.

2. The pharmaceutical composition defined in claim 1 in the form of a annular tablet and a molded tablet.

3. The pharmaceutical composition defined in claim 2 wherein the annular tablet is comprised of one or more layers containing the pharmaceutically active ingredient capable of oral administration.

4. The pharmaceutical composition defined in claim 2 wherein the tablet contains a therapeutically effective amount of at least one pharmaceutically active ingredient capable of intraoral administration and one or more pharmaceutically acceptable excipients for intraoral administration.

5. The pharmaceutical composition defined in claim 2 wherein the tablet is formulated with a pharmaceutically acceptable effervescent agent capable of generating effervescence when contacted with saliva.

6. The pharmaceutical composition as defined in claim 1 where the annular tablet may be film coated and may contain a pharmaceutically acceptable flavoring agent.

7. The pharmaceutical composition defined in claim 3 wherein the tablet is an immediate drug release tablet comprising at least one pharmaceutically active ingredient capable of oral administration and one or more pharmaceutically acceptable excipients for oral administration.

8. The pharmaceutical composition defined in claim 3 wherein the tablet comprises more than one layer including a sustained release layer containing a therapeutically effective amount of a first pharmaceutically active ingredient capable of oral administration and optionally including an immediate release layer containing a therapeutically effective amount of a second pharmaceutically active ingredient capable of oral administration, same or different from the first.

9. The pharmaceutical composition defined in claim 3 wherein the tablet comprises more than one layer comprising the pharmaceutically active ingredient capable of oral administration and where at least one of the layers comprising the pharmaceutically active ingredient capable of oral administration is an immediate drug release layer.

10. The pharmaceutical composition defined in claim 8 where the tablet provides sustained release of the pharmaceutical active ingredient capable of oral administration for a period of 0.5 to 24 hours.

11. The pharmaceutical composition defined in claim 10 wherein the tablet is formulated by incorporating or coating the pharmaceutically active ingredient with one or more pharmaceutically acceptable sustained released polymers.

12. The pharmaceutical composition defined in claim 11 wherein the one or more pharmaceutically acceptable sustained release polymer is selected from the group consisting of methylcellulose, hydroxypropyl methylcellulose, ethyl cellulose, cellulose acetate phthalate, acacia, gums, wax, glycerol monostearate, acrylic acid polymers and copolymers, methacrylic acid, methyl acrylate, ethyl acrylate, methyl methacrylate, ethyl methacrylate, and ion exchange resins capable of forming a sustained release ion-exchange resin-drug complex.

13. The pharmaceutical composition defined in claim 3 wherein the tablet comprises a therapeutically effective amount of one or more pharmaceutically active ingredients capable of oral administration in a delayed release form which delays the release of the one or more pharmaceutically active ingredients capable of oral administration for a period of 0.5 to 12 hours.

14. The pharmaceutical composition defined in claim 13 wherein the tablet comprising a therapeutically effective amount of one or more pharmaceutically active ingredients capable of oral administration in a delayed release form includes a delayed release coating on the one or more pharmaceutically active ingredients, the delayed release coating comprising one or more pharmaceutically acceptable polymers selected from the group consisting of methyl cellulose, hydroxypropyl cellulose, hydroxyethyl cellulose, hydroxymethyl cellulose, hydroxypropyl methyl cellulose acetate succinate, ethyl cellulose, cellulose acetate phthalate, hydroxypropyl methylcellulose phthalate, cellulose acetate trimellitate, carboxymethylcellulose sodium, acrylic acid polymers and copolymers, polymers or copolymers of methacrylic acid, methyl acrylate, ethyl acrylate, methyl methacrylate, ethyl methacrylate, vinyl acetate, vinyl acetate phthalate, an azo compound, polyvinyl pyrrolidone, pectin, amylose, shellac, zein, and guar gum.

15. The pharmaceutical composition defined in claim 3 wherein the tablet is chewable and comprises one or more pharmaceutically acceptable excipients suitable for a chewable medication and a flavoring agent.

16. The pharmaceutical composition defined in claim 1 wherein the tablet containing the pharmaceutically active ingredient capable of oral administration remains substantially intact until the intraoral administration of the pharmaceutically active ingredient capable of intraoral administration has been completed.

17. The pharmaceutical composition defined in claim 1 wherein the pharmaceutically active ingredient capable of intraoral administration has a rapid onset of the desired therapeutic effect through intraoral absorption.

18. The pharmaceutical composition defined in claim 1 wherein the pharmaceutically active ingredient capable of intraoral administration is selected from the group consisting of analgesics, antihistamines, antidiarrheal, anxiolytic, hypnotics, stimulants, cardiovascular drugs, pulmonary drugs, antihypertensives, antiemetics, anti-inflammatory drugs, renal drugs, steroids, drugs for neurological disorders, antipsychotic drugs, drugs for treating endocrine disorders, drugs for promoting immunology, drugs for treating osteoarthritis, drugs for treating glaucoma, drugs for treating allergic rhinitis, drugs for treating anemias and other hematological disorders, drugs for treating infectious diseases, drugs for the treatment and symptoms of cancer, drugs for insomnia, and antidiabetic drugs.

19. A method of administering a pharmaceutical composition in unit dosage form as a tablet for both intraoral and oral administration to a patient, which comprises: (a) as a first releasing portion, a tablet comprising a therapeutically effective amount of at least one pharmaceutically active ingredient capable of intraoral administration having a molecular weight of less than 350 Daltons in a dosage of no more than 50 mg; and (b) as a second releasing portion located around the first portion, a therapeutically effective amount of at least one pharmaceutically active ingredient capable of oral administration and which is releasable and orally ingestible by the patient after the tablet has disintegrated or has dissolved intraorally, which comprises the steps of: (i) placing the pharmaceutical composition under the tongue or against the inner wall of the cheek or within the vestibular mucosa of said patient; (ii) retaining the pharmaceutical composition under the tongue or against the inner wall of the cheek or vestibular mucosa of the patient until the first releasing portion of the pharmaceutical composition containing the pharmaceutically active ingredient capable of intraoral administration has dissolved or has disintegrated thereby substantially releasing the pharmaceutically active ingredient capable of intraoral administration, wherein the first releasing portion disintegrates or dissolves within 10 minutes permitting rapid release and uptake of the pharmaceutically active ingredient with in the oral region; and (iii) following step (ii) sucking or swallowing whole or chewing and swallowing the second releasing portion of the pharmaceutical composition.

20. The pharmaceutical composition defined in claim 1 wherein the pharmaceutically active ingredient capable of intraoral administration has a first pass metabolism which is avoided by intraoral administration.

21. The pharmaceutical composition defined in claim 1 wherein the pharmaceutically active ingredient capable of intraoral administration has a rapid onset of desired therapeutic effect through intraoral absorption.

* * * * *